(12) United States Patent
Wang et al.

(10) Patent No.: US 9,400,176 B2
(45) Date of Patent: Jul. 26, 2016

(54) DYNAMIC FOCUS ADJUSTMENT WITH OPTICAL HEIGHT DETECTION APPARATUS IN ELECTRON BEAM SYSTEM

(71) Applicant: Hermes Microvision, Inc., Hsinchu (TW)

(72) Inventors: Joe Wang, Campbell, CA (US); Van-Duc Nguyen, Fremont, CA (US); Yi-Xiang Wang, Fremont, CA (US); Jack Jau, Los Altos Hills, CA (US); Zhong-Wei Chen, San Jose, CA (US)

(73) Assignee: HERMES MICROVISION, INC., Hsinchu (TW)

( * ) Notice: Subject to any disclaimer, the term of this patent is extended or adjusted under 35 U.S.C. 154(b) by 1 day.

(21) Appl. No.: 14/306,298

(22) Filed: Jun. 17, 2014

(65) Prior Publication Data

US 2014/0291517 A1    Oct. 2, 2014

Related U.S. Application Data

(63) Continuation of application No. 12/764,902, filed on Apr. 21, 2010, now Pat. No. 8,791,414.

(51) Int. Cl.
G01N 23/00 (2006.01)
G01B 11/22 (2006.01)
G01N 23/04 (2006.01)
G01N 23/20 (2006.01)
H01J 37/21 (2006.01)
H01J 37/28 (2006.01)

(52) U.S. Cl.
CPC ............... *G01B 11/22* (2013.01); *G01N 23/04* (2013.01); *G01N 23/20058* (2013.01); *H01J 37/21* (2013.01); *H01J 37/28* (2013.01); *G01N 2223/32* (2013.01); *G01N 2223/3301* (2013.01); *G01N 2223/3302* (2013.01); *G01N 2223/646* (2013.01); *H01J 2237/216* (2013.01); *H01J 2237/2482* (2013.01); *H01J 2237/2487* (2013.01)

(58) Field of Classification Search
None
See application file for complete search history.

(56) References Cited

U.S. PATENT DOCUMENTS

| 4,218,621 A | * | 8/1980 | Nakasuji | H01J 37/3007 250/396 R |
|---|---|---|---|---|
| 6,107,637 A | * | 8/2000 | Watanabe | B82Y 10/00 250/208.1 |
| 6,333,510 B1 | * | 12/2001 | Watanabe | B82Y 10/00 250/559.27 |
| 7,041,976 B1 | * | 5/2006 | Neil | G01R 31/307 250/310 |

(Continued)

FOREIGN PATENT DOCUMENTS

| DE | WO 2009062929 | * | 5/2009 | ......... G02B 21/0004 |
|---|---|---|---|---|
| DE | WO 2009062929 | * | 9/2010 | ......... G02B 21/0004 |

(Continued)

*Primary Examiner* — Andrew Smyth
(74) *Attorney, Agent, or Firm* — WPAT, PC; Justin King

(57) ABSTRACT

The present invention generally relates to dynamic focus adjustment for an image system. With the assistance of a height detection sub-system, present invention provides an apparatus and methods for micro adjusting an image focusing according the specimen surface height variation by altering the field strength of an electrostatic lens between objective lens and sample stage/or a bias voltage applied to the sample surface. Merely by way of example, the invention has been applied to a scanning electron inspection system. But it would be recognized that the invention could apply to other system using charged particle beam as observation tool with a height detection apparatus.

13 Claims, 6 Drawing Sheets

(56) References Cited

U.S. PATENT DOCUMENTS

| | | | | | |
|---|---|---|---|---|---|
| 7,173,243 | B1* | 2/2007 | Yang | ............... | H01J 37/28 250/307 |
| 7,767,982 | B2* | 8/2010 | Wang | ............... | G02B 7/32 250/310 |
| 8,530,856 | B2* | 9/2013 | Spruck | ............... | G02B 21/0004 250/310 |
| 2002/0053634 | A1* | 5/2002 | Watanabe | ............... | B82Y 10/00 250/201.2 |
| 2002/0149381 | A1* | 10/2002 | Lo | ............... | G01R 31/307 324/754.22 |
| 2003/0007677 | A1* | 1/2003 | Hiroi | ............... | G06T 7/001 382/149 |
| 2003/0062479 | A1* | 4/2003 | Kametani | ............... | H01J 37/28 250/310 |
| 2003/0141451 | A1* | 7/2003 | Sato | ............... | G01N 23/22 250/310 |
| 2004/0154744 | A1* | 8/2004 | Kaito | ............... | G01N 1/32 156/345.24 |
| 2004/0165167 | A1* | 8/2004 | Imai | ............... | G03F 7/708 355/53 |
| 2004/0217287 | A1* | 11/2004 | Watanabe | ............... | B82Y 10/00 250/310 |
| 2005/0242286 | A1* | 11/2005 | Watanabe | ............... | B82Y 10/00 250/310 |
| 2006/0060781 | A1* | 3/2006 | Watanabe | ............... | B82Y 10/00 250/310 |
| 2006/0203232 | A1* | 9/2006 | Okita | ............... | G03F 1/84 356/237.2 |
| 2008/0078933 | A1* | 4/2008 | Watanabe | ............... | B82Y 10/00 250/307 |
| 2008/0302974 | A1* | 12/2008 | Wang | ............... | G02B 7/32 250/442.11 |
| 2009/0208091 | A1* | 8/2009 | Hayakawa | ............... | G01N 21/956 382/149 |
| 2009/0309022 | A1* | 12/2009 | Gunji | ............... | G01N 23/2251 250/307 |
| 2010/0193686 | A1* | 8/2010 | Watanabe | ............... | B82Y 10/00 250/307 |
| 2010/0224780 | A1* | 9/2010 | Spruck | ............... | G02B 21/0004 250/309 |
| 2012/0157324 | A1* | 6/2012 | Lizardi | ............... | C12Q 1/6886 506/2 |

FOREIGN PATENT DOCUMENTS

| | | | |
|---|---|---|---|
| WO | WO 2009062929 A2 * | 5/2009 | |
| WO | WO 2009062929 A3 * | 9/2010 | |

\* cited by examiner

DYNAMIC FOCUS ADJUSTMENT WITH OPTICAL HEIGHT DETECTION APPARATUS IN ELECTRON BEAM SYSTEM

CROSS-REFERENCE TO RELATED APPLICATIONS

This application is a continuation of U.S. application Ser. No. 12/764,902, filed on Apr. 21, 2010, the entire contents of which are incorporated herein by reference.

FIELD OF THE INVENTION

The present invention generally relates to an electron beam system, and more particularly to a device for dynamic measuring height variation of a specimen to be inspected by a tool and a method for dynamic adjusting the focus of an electron beam image while inspecting a specimen.

BACKGROUND OF THE INVENTION

As semiconductor devices move toward higher integration and density with advances in semiconductor materials and processes, the critical defect size becomes smaller. This requires defect inspection tool, especially Electron Beam (e-beam) defect inspection tool has higher resolution and higher inspection speed. Thus, more accurate and fast auto-focus ability becomes more important.

A typical e-beam defect inspection tool projects electron beam onto the suspected area, collects the scattered or reflected electrons emanated form the surface of a specimen to form image of the inspected area, and then exports the position of the image anomalies. In order to have a good quality of surface image, the resolution of the inspection tool and the ability to keep good focus status. Higher resolution results in small depth of focus (DOF), thus require better and faster focus control capability.

After a sharp image is acquired from an wafer surface by using, for example e-beam inspection tool, anomaly analysis requires a lot of image processing techniques. There are several factors affect wafer surface topology for example vertical position and tilt angle. However, the most important three may be first, the wafer intrinsic flatness; second, the IC manufacturing induced surface tension and surface roughness; and third, the processing tool for example wafer chuck or x-y translation stage induced wafer warping and tilting. The surface topology is easy to cause the image off focus if no support of auto focus/work distance control system. Without precise knowledge of the vertical position and dynamic adjustment, the image will be blurred due to not enough DOF and surface topology variation. To present a sharp image while performing continuous inspection, the e-beam system has to adjust the magnetic field of the objective lens in time by changing the current flow through the coil of the objective lens. However, because of the hysteresis effect, the responding time of altering the focus by varying the lens current is too slow compared to the sample moving speed; thus the acquired image is obscure after image processing. Example of varying focus current is illustrated in U.S. Pat. No. 5,502,306 to Meisburger et al. The optimum focus current of a few designated points on specimen is determined in the initialization stage and for any points in between these one may interpolate the desired focus current. Another method to keep the image sharp was disclosed in U.S. Pat. No. 7,041,976 by Neil et al. The method automatically focuses an electron image by varying wafer surface bias which is correspondingly determined by the energy filter cut-off voltage of the scattered electrons.

Systems used to manufacture semiconductor devices such as processing tools, metrology tools, and inspection tools may include a height sensor as a focusing sub-system. A height sensor may be used to position a wafer within a system prior to or within the processing of the wafer. Height sensors may be used in different configurations for different applications.

Example of height sensor as illustrated in U.S. Pat. No. 4,538,069 to Shambroom et al. utilizes capacitance height sensor in lithography machine. The control system appropriately adjusts the deflection angle of the electron beam in response to the detected deviation to write at the desired point of the reticle with a very high degree of accuracy. However, the accurate reading of the capacitance gage requires a uniform specimen material. The complicate material compositions on a semiconductor wafer become a disadvantage of capacitance gage. Some height sensors detect the scattered light and convert the detected light into electrical signals that may be measured to provide height information. Examples of such height sensors are illustrated in U.S. Pat. No. 5,585,629 to Doran et al. Determine position deviation with dual beam optical LED. Output from the system enable adjustment of fine positioning stage; U.S. Pat. No. 6,333,510 to Watanabe et al. Determine height with dual beam optical system and apply the scale factor to adjust the focus of objective lens, and U.S. patent application Ser. No. 11/759,138 to Wang et al, Determine height with an optical system and adjust focal point by controlling Piezo-electric of the stage. All of which are incorporated by reference as if fully set forth herein. The disadvantage of implement height variation to adjust stage motion in vertical direction is that motions become a new vibration source of the imaging system. And the disadvantage of implement height variation to adjust objective lens exciting current is slow due to the hysteresis effect of the magnetic field in the objective lens.

The object of the present invention is to provide methods and apparatus to avoid the stage motion on the vertical direction and introduce a fast responded electrostatic field during dynamic focusing for wafer continuous e-beam defect inspection.

BRIEF SUMMARY OF THE INVENTION

The present invention generally relates to dynamic focus adjustment for an image system. With the assistance of a height detection sub-system, present invention provides an apparatus and methods for micro adjusting an image focusing according the specimen surface height variation by altering the field strength of an electrostatic lens between objective lens and sample stage/or a bias voltage applied to the sample surface. Merely by way of example, the invention has been applied to a scanning electron inspection system. But it would be recognized that the invention could apply to other system using charged particle beam as observation tool with a height detection apparatus.

The height sensing apparatus of the present invention was adopted from Wang et al. U.S. patent application Ser. No. 11/759,138, filed Jun. 6, 2007. According to an embodiment of the present invention, the control signal in voltage convert from the height variation is sent to an electrode between the objective lens and the sample stage. The electrode is acted as an electrostatic lens to micro-adjust the focus point of the primary beam.

According to another embodiment of the present invention, the control signal in voltage convert from the height variation is sent to the sample stage. The specimen surface bias is varied according to the control signal. Thus varies the landing energy of the incident electrons thereafter varies the focus point of the primary beam.

This invention provides an electron beam system, which comprises an electron source for emitting a primary beam, a condenser lens for condense the primary beam, an objective lens for focusing the primary beam on a surface of a specimen, and means for measuring height variation of the specimen. The means for measuring height variation of the specimen comprises an optical illuminating source for emitting light on the specimen, a detecting unit for receiving image of grating reflected from the specimen, and means for varying landing energy of the primary beam. The means for varying landing energy of the primary beam may comprise means for calculating focus of the tool, means for calculating bias of the specimen surface, and means for controlling bias of the specimen surface. The means for varying landing energy of the primary beam may also comprise means for calculating focus of the tool, means for calculating electrostatic strength of the control electrode which includes scanning correction, image rotation compensation, image magnification compensation, image shifting compensation, and means for controlling electrostatic strength of the control electrode.

This invention also provides a device for measuring height variation of a specimen to be inspected by a tool, which comprise an optical illuminating source for emitting light on the specimen, a detecting unit for receiving image of grating reflected from the specimen, means for calculating focus of the tool, means for calculating bias of the specimen surface which includes scanning correction, image rotation compensation, image magnification compensation, image shifting compensation, and means for controlling bias of the specimen surface.

This invention still provides a device for adjusting focus of an electron beam in a scanning electron microscope (SEM), which comprises an optical height detection unit for detecting a surface of a specimen to be inspected by the SEM and outputting signals of height variation information, a SEM focus control unit for receiving the signals of height variation information, calculating focus, and outputting signals of focus adjusting information, and a SEM focusing unit for focusing the electron beam of the SEM on the surface of the specimen according to the signals of focus adjusting information, wherein said SEM focusing unit is selected from the group consisting of means for adjusting bias of the specimen's surface, a control electrostatic lens, and a condenser lens.

This invention further provides a method for dynamic adjusting the focus of an electron beam image while inspecting a specimen, which comprises steps of providing an electron beam inspection system, wherein a control electrode is configured to the system and then providing an optical illumination flux through a pattern plate and a lens to a surface of a specimen to project a pattern onto the surface of the specimen, the pattern being associated with the pattern plate. The illumination flux reflected from the surface of the specimen is detected with a detector. Information associated with the detected illumination flux is then processed. Next, optical images based on at least information associated with the detected illumination flux are generated, wherein the first image includes a first image part for the pattern and a second image part for the specimen. The local height variation of the surface of the specimen within the electron beam field of view according to the position variation of the pattern between these optical images is then determined. The height variation is compared with the depth of focus of the electron beam image. Correction factors are calculated to compensate the height variation respect to the depth of focus of the electron beam image within the field of view. A control signal is generated based on at least information associated with these optical images. The control signal is then provided to the control object. The focus of the electron beam image of the specimen is adjusted in response to the control signal that apply to the control object, and an electron beam inspection for the specimen with the new focus length is performed.

DETAILED DESCRIPTION OF THE INVENTION

The present invention generally relates to dynamic focus adjustment for an image system. With the assistance of a height detection system, present invention provides an apparatus and methods for micro-adjusting an image focus according the specimen surface height variation by altering the field strength of an electrostatic lens between objective lens and sample stage or by altering a bias voltage applied to the sample surface. Merely by way of example, the invention has been applied to a scanning electron inspection system. But it would be recognized that the invention could apply to other systems using charged particle beam as observation tool with a height detection apparatus.

Figure 1A:
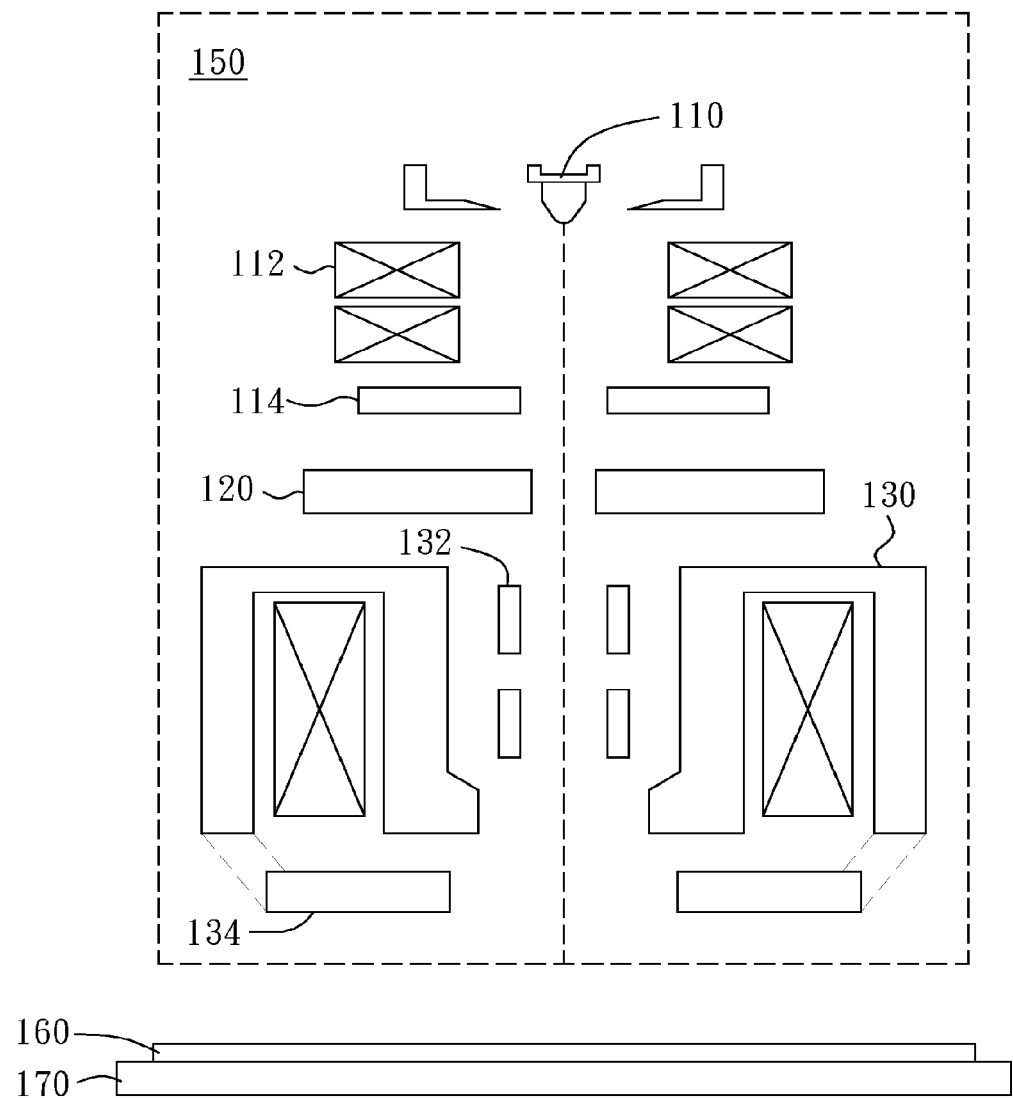
FIG. 1A is a system configuration drawing of an improved Swing Objective Retarding Immersion Lens (SORIL) system disclosed by Chen et al. in U.S. patent application Ser. No. 12/257,304
Figure 1B:
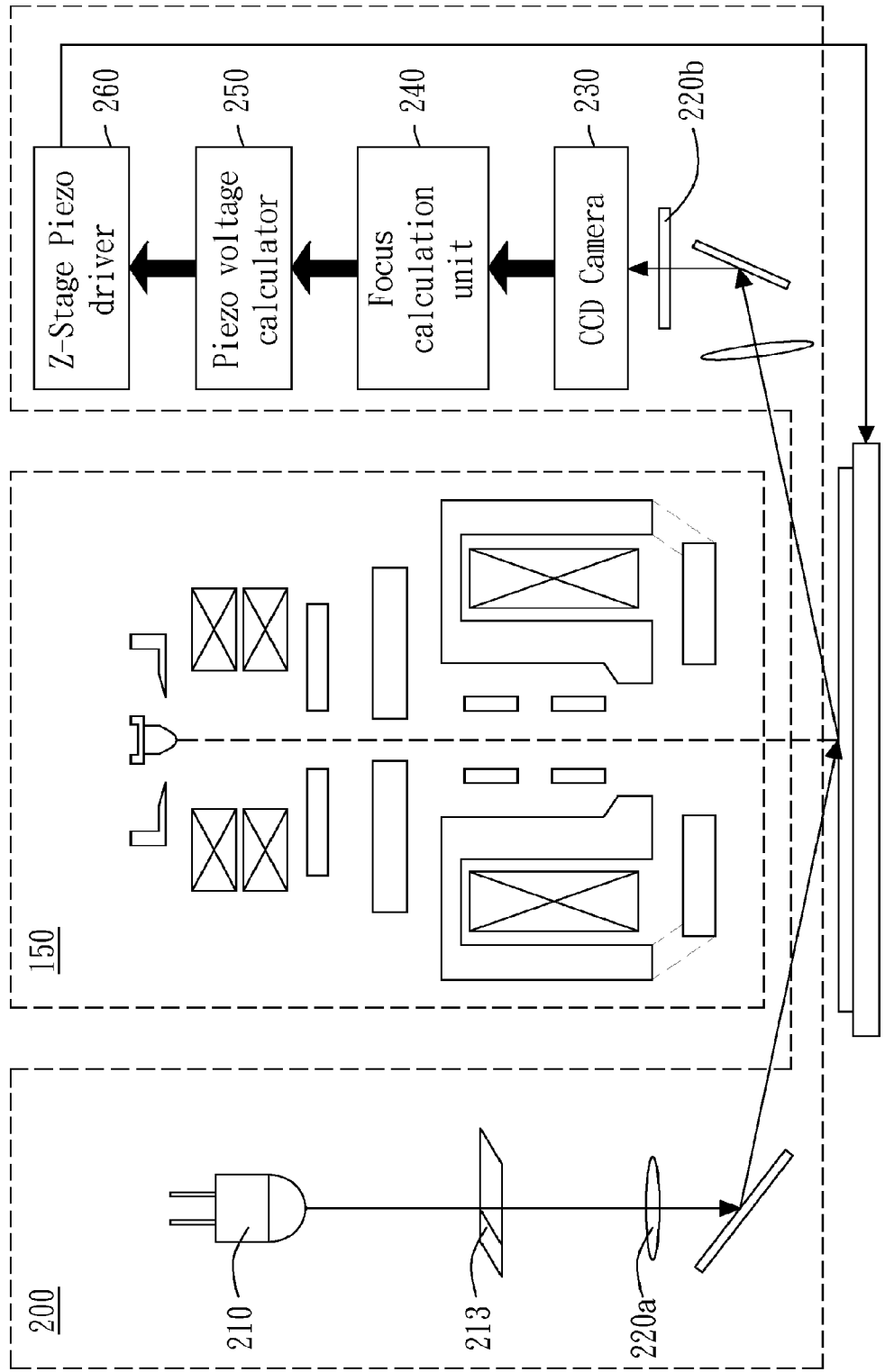
FIG. 1B is a system configuration drawing of a prior art e-beam system with height sensor sub-system that disclosed by Wang et al in U.S. patent application Ser. No. 11/759,138.

The system configuration of the present invention is illustrated in FIG. 1A and FIG. 1B which includes a regular e-beam inspection system 150 to perform inspection and a height detection sub-system 200 to assist focusing. Detail of the e-beam system 150 comprises electron source 110, condenser lens 112, aperture 114, detector 120, objective lens 130, deflectors 132, and control electrode 134. A primary electron beam generates from electron source 110 is focused into an electron beam probe by the objective lens 130, that scans across a specimen 160 hold by the sample stage 170, such as E-chuck. Specimen 160 may be, but not limited to, a wafer such as a substrate used for fabricating semiconductor devices. The detector 120 collects the secondary electrons emanating from the specimen 160 surface to form an electron beam image after processing. The e-beam system 150 may be, for example, an improved Swing Objective Retarding Immersion Lens (SORIL) system disclosed by Chen et al. in U.S. patent application Ser. No. 12/257,304 "An Electron Beam Apparatus" filed in Oct. 23, 2008.

The height detection sub-system 200 is adopted from Wang et al. U.S. patent application Ser. No. 11/759,138, filed Jun. 6, 2007. The height detection sub-system 200 comprises an illumination light source 210, a light pattern plate 213, optical mirror system 220a and 220b, an optical detection unit 230, an optical image processing unit 240, a control signal generating unit 250, and a control action driver 260. The illuminated flux from the light source 210 projects the line grating on the light pattern plate 213 through condenser lens and reflecting mirror of the optical mirror system 220a onto specimen 160 surface. The reflected line grating image from the specimen 160 surface is passed through reflecting mirror and filter of the optical mirror system 220b into the optical detection unit 230. The optical detection unit 230 may be, but not limited to, a CCD or CMOS camera. A series of line grating images received from CCD camera is processed in an optical image process unit 240. These images are taken while the SORIL system is performing surface inspection. The optical image processing unit 240 compares the position of the line grating on these optical images and calculates the height variation of each image that caused by surface topology then passes the result to control signal generating unit 250. The local focus variation of the electron inspection image is corresponding to the surface height variation due to topology. The control signal generating unit 250 intrinsically is a high speed computer, based on the focus variation converted from each image, so the computer will decide if these variations are within the acceptable depth of focus. If it is not acceptable then the computer calculates correction actions control signal for the controlled objective. For example, calculates the piezo-voltage for stage motion control, calculates electrostatic lens strength for control electrodes and the voltage bias that apply to the specimen surface. Finally the correction signal is sent to the controlled objective through the control driver 260.

Figure 2A:
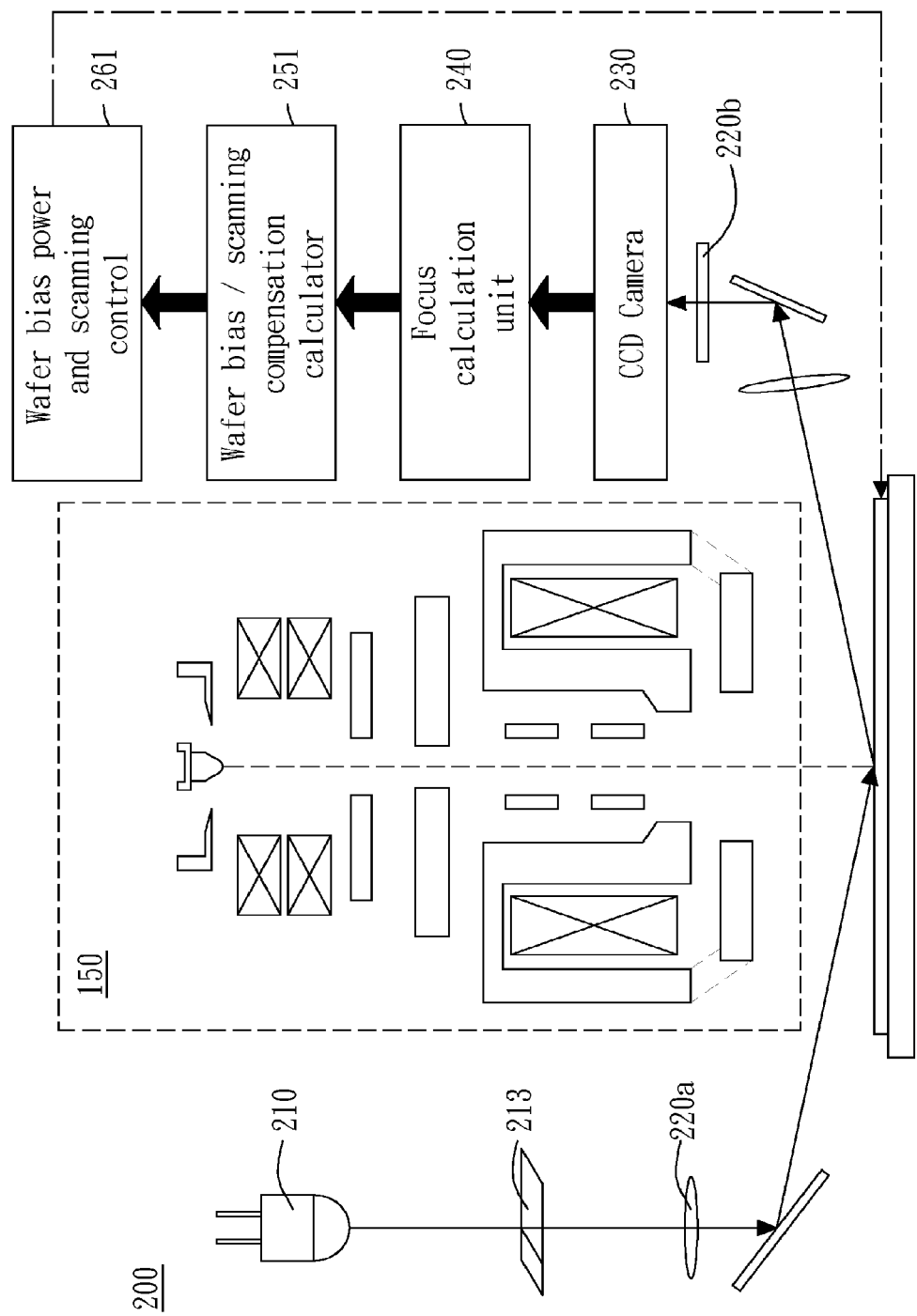
FIG. 2A is a diagrammatic representation of an e-beam system with height sensor sub-system, where the control signal is sent to vary the specimen surface bias according to an embodiment of present invention.
Figure 2B:
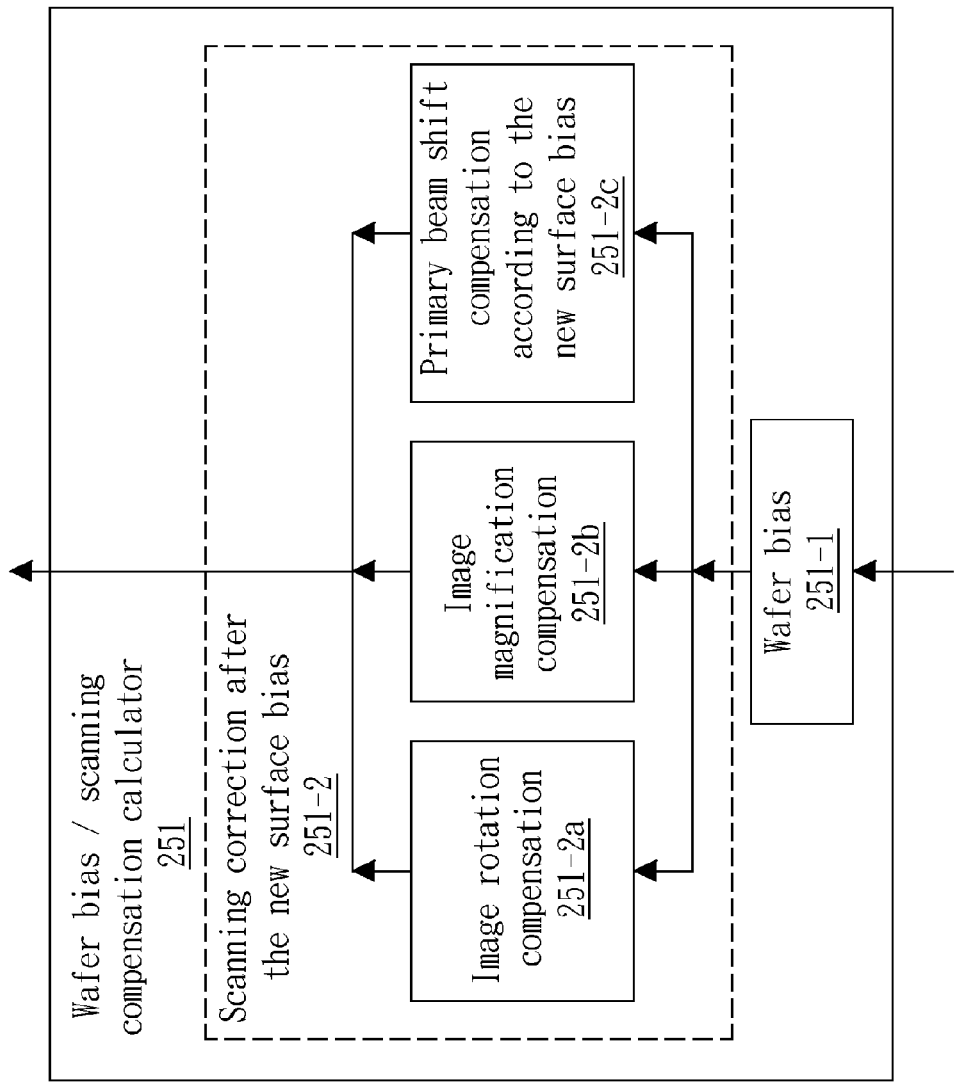
FIG. 2B is a diagrammatic representation of a wafer bias/scanning compensation calculator according to an embodiment of present invention.

As most of the prior arts disclosed, in order to have a sharp image for defects inspection, the correct signal converted from height variation were sent to activate stage motion in the direction of light axis for compensating the focus deviation due to surface topology. However, according to Zhang disclosed in U.S. patent application Ser. No. 12/397,042 filed in Mar. 3, 2009, the motion of the stage is one of the most significant noise sources that interfering the sharpness of an image. Therefore, in order to have a quality inspection image, the motion of stage during micro focus deviation compensation should be avoided as possible, According to one embodiment of the present invention illustrates in FIG. 2A, the control signal for the control driver 261 is sent to vary the specimen surface bias instead of stage motion. Varying the specimen bias will alter the landing energy of the primary beam, thereafter varies the primal focus length that originally set by the objective lens 130. The optical image processing unit 240 compares the position of the line grating on these optical images and calculates the height variation of each image that caused by surface topology then passes the result to control signal generating unit 251. The control signal generating unit 251, base on the focus variation of each image, decides if these variations are within the acceptable depth of focus or not. The control signal generating unit 251 calculates the surface bias needed to apply on the specimen surface and passes the signal to the control driver 261. The calculation, as shown in FIG. 2B, also includes a scanning correction after the new surface bias calculated 251-1 is implemented. The scanning correction calculation 251-2 includes image rotation compensation 251-2a, image magnification compensation 251-2b, and primary beam shift compensation according to the new surface bias 251-2c. The control driver 261 send out control signal to vary the wafer surface bias that could bring the off-focused electron beam image due to surface topology back to acceptable DOF.

Figure 3A:
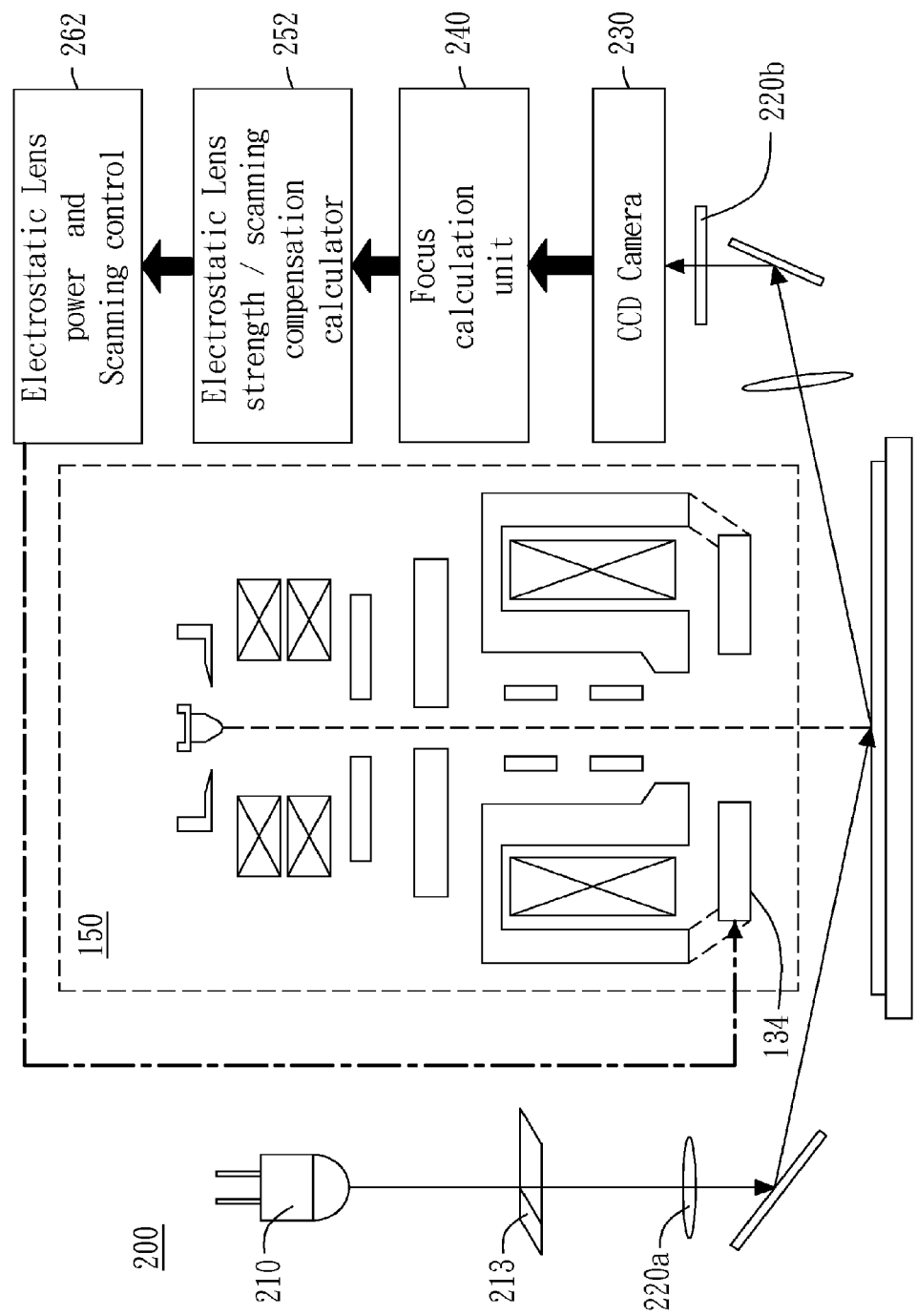
FIG. 3A is a diagrammatic representation of an e-beam system with height sensor sub-system, where the control signal is sent to a pair of electrodes between the objective lens and the sample stage according to an embodiment of present invention.
Figure 3B:
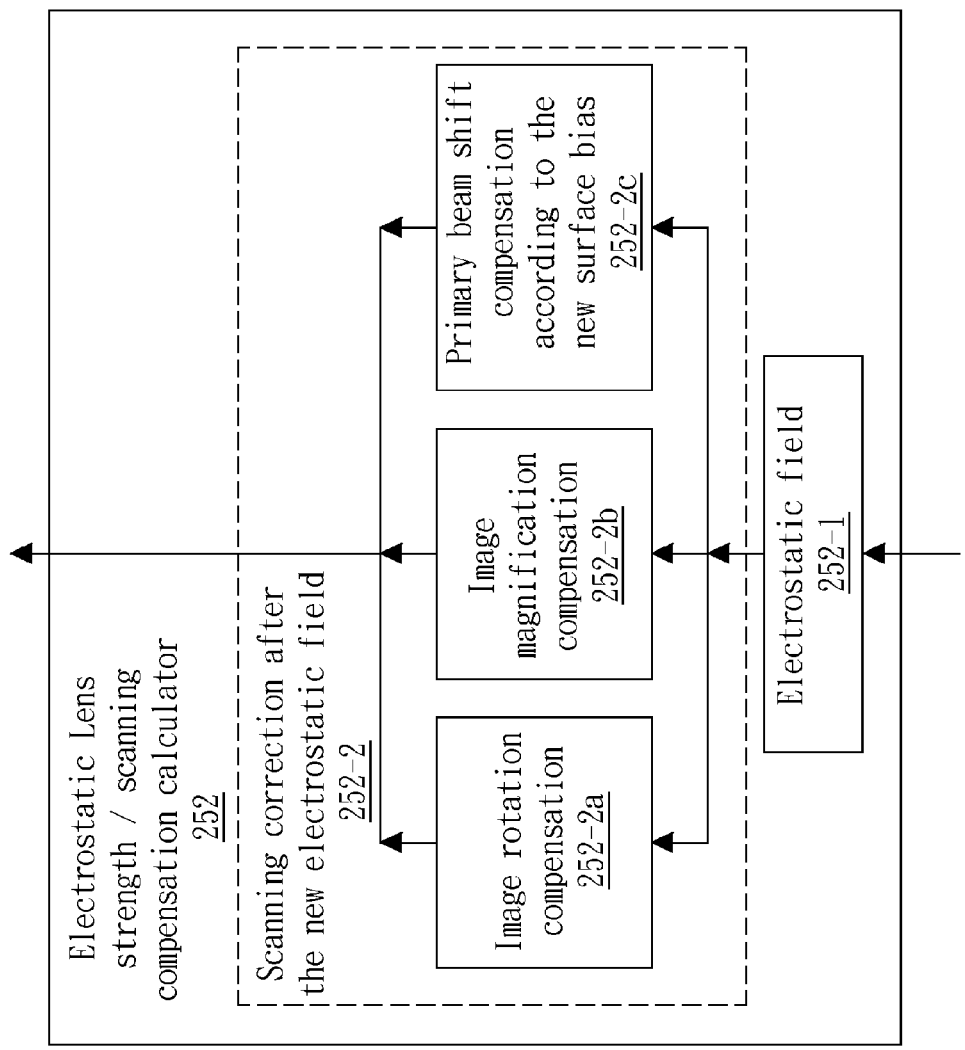
FIG. 3B is a diagrammatic representation of an electrostatic lens strength/scanning compensation calculator according to an embodiment of present invention.

FIG. 3 illustrates another embodiment of the present invention. The control signal for the control driver 262 is sent to vary the electrostatic field strength of the control electrode 134 instead of stage motion. The control electrode 134, which is a single plate with a central hole to allow the primary beam passing therethrough, is acting as an electrostatic lens between the objective lens and specimen surface. Varying the electrostatic field strength of control electrode 134 will alter the primal focus length that originally set by the objective lens. The optical image processing unit 240 compares the position of the line grating on these optical images and calculates the height variation of each image that caused by surface topology then passes the result to control signal generating unit 252. The control signal generating unit 252, based on the focus variation of each image, decides if these variation are within the acceptable depth of focus or not. The control signal generating unit 252 calculates the voltage that needs to apply on the control electrode 134 for the proper electrostatic field strength and passes the signal to the control driver 262. The calculation, as shown in FIG. 3B, also includes a scanning correction after the new electrostatic field strength calculated 252-1 is applied. The scanning calculation correction 252-2 includes image rotation compensation 252-2a, image magnification compensation 252-2b, and primary beam shift compensation according to the new electrostatic field strength 252-2c. The control driver 262 sends out control signals to vary the voltage of the control electrode 134 that could bring the off-focused electron beam image due to surface topology back to acceptable DOF.

The control electrode 134, or the control electrostatic lens, could be presented between the objective lens and specimen surface in many forms. In present invention, for example, the control electrode 134 is on the extension of outer pole piece of the SORIL lens. One embodiment suggests that position the control electrostatic lens as one pair of deflector electrodes. The benefit of this configuration is that could have more compact structure due to the dual function design.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A device for dynamic measuring height variation of a specimen to be inspected by a tool, comprising:
    an optical illuminating source for emitting light on the specimen;
    a detecting unit for receiving light reflected from the specimen;
    means for calculating a focus of the tool;
    means for calculating bias of the specimen surface to a voltage according to the focus and scanning compensation while the specimen is inspected by a charged particle beam; and
    means for controlling bias of the specimen surface to the voltage.

2. The device for dynamic measuring height variation according to claim 1, further comprising an optical system for the optical illuminating source and the detecting unit.

3. The device for dynamic measuring height variation according to claim 1, wherein the means for calculating bias of the specimen surface and scanning compensation includes:
   image rotation compensation;
   image magnification compensation; and
   primary beam shift compensation.

4. An electron beam system, comprising:
   an electron source for emitting a primary beam;
   a condenser lens for condense the primary beam;
   an objective lens for focusing the primary beam on a surface of a specimen; and
   means for dynamically measuring height variation of the specimen;
   wherein the means for measuring height variation of the specimen comprises an optical illuminating source for emitting light on the specimen, a detecting unit for receiving light reflected from the specimen, and means for calculating bias of the surface of the specimen to a voltage according to a focus and controlling bias of the surface of the specimen to the voltage while the specimen is inspected by the primary electron beam.

5. The electron beam system according to claim 4, wherein the means for varying landing energy of the primary beam comprises:
   means for calculating focus of the tool;
   means for calculating bias of the specimen surface and scanning compensation; and
   means for controlling bias of the specimen surface.

6. The electron beam system according to claim 5, wherein the means for calculating bias of the specimen surface and scanning compensation includes:
   image rotation compensation;
   image magnification compensation; and
   primary beam shift compensation.

7. The electron beam system according to claim 4, wherein the means for varying landing energy of the primary beam comprises:
   means for calculating focus of the tool;
   means for calculating electrostatic strength of a control electrode and scanning compensation; and
   means for controlling electrostatic strength of the control electrode.

8. The electron beam system according to claim 7, wherein the means for calculating electrostatic strength of a control electrode and scanning compensation includes:
   image rotation compensation;
   image magnification compensation; and
   primary beam shift compensation.

9. The electron beam system according to claim 4, further comprising an optical system for the optical illuminating source and the detecting unit.

10. The electron beam system according to claim 4, further comprising a deflection unit for deflecting the primary beam and scanning on the specimen.

11. The electron beam system according to claim 10, further comprising a detector for receiving signal electrons from the specimen.

12. The electron beam system according to claim 11, further comprising a control electrode, between the objective lens and the specimen, on extension of outer pole pieces of the objective lens.

13. A device for dynamically adjusting focus of an electron beam in a scanning electron microscope (SEM), said device comprising:
   an optical height detection unit for detecting a surface of a specimen to be inspected by the SEM and outputting signals of height variation information;
   a SEM focus control unit for receiving the signals of height variation information, calculating a focus, and outputting signals of focus adjusting information; and
   a SEM focusing unit for focusing the electron beam of the SEM on the surface of the specimen according to the signals of focus adjusting information,
   wherein said SEM focusing unit comprises
   means for adjusting bias of the specimen's surface via calculating bias of the specimen's surface to a voltage according to the focus and controlling bias of the specimen's surface to the voltage while the specimen is inspected by the SEM, and
   wherein said SEM focusing unit is selected from the group consisting of
   a control electrostatic lens, and
   a condenser lens,
   the control electrostatic lens being a plate with a central hole to allow passage of a primary beam of the SEM therethrough, wherein the control electrode lens is under an objective lens of the SEM.

* * * * *